US012177303B2

(12) United States Patent
Ramchandran et al.

(10) Patent No.: US 12,177,303 B2
(45) Date of Patent: Dec. 24, 2024

(54) MULTI-VERSION PROCESSING USING A MONITOR SUBSYSTEM

(71) Applicant: Illumina, Inc., San Diego, CA (US)

(72) Inventors: Padmanabhan Ramchandran, San Diego, CA (US); Ian Patrick Hurst, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 18/367,762

(22) Filed: Sep. 13, 2023

(65) Prior Publication Data

US 2024/0098152 A1 Mar. 21, 2024

Related U.S. Application Data

(60) Provisional application No. 63/408,235, filed on Sep. 20, 2022.

(51) Int. Cl.
*H04L 67/00* (2022.01)
*G06F 8/71* (2018.01)
*H04L 41/082* (2022.01)

(52) U.S. Cl.
CPC .............. *H04L 67/34* (2013.01); *G06F 8/71* (2013.01); *H04L 41/082* (2013.01)

(58) Field of Classification Search
CPC .......... H04L 67/34; H04L 41/082; G06F 8/71
See application file for complete search history.

(56) References Cited

U.S. PATENT DOCUMENTS

| 6,047,045 | A | * | 4/2000 | Bauer | H04Q 3/005 379/26.01 |
| 8,296,599 | B1 | * | 10/2012 | Boyer | G06F 11/2046 714/4.11 |
| 9,288,225 | B1 | * | 3/2016 | Fei | H04L 63/1441 |
| 2002/0083199 | A1 | * | 6/2002 | Dingsor | H04L 67/1008 709/225 |

(Continued)

FOREIGN PATENT DOCUMENTS

CN 102521001 B 4/2014

OTHER PUBLICATIONS

"Conditional Access Policy—Block Legacy Authentication", Techlabs, May 30, 2021, 40 pages.

(Continued)

*Primary Examiner* — Andrew C Georgandellis
(74) *Attorney, Agent, or Firm* — Flaster Greenberg P.C.

(57) ABSTRACT

Versions of a sequencing system may be monitored to enable changing of a version of a server subsystem operating the sequencing system to service requests from client subsystems for performing analysis of sequencing data. A monitor subsystem may be utilized for receiving and authorizing requests from client subsystems. The monitor subsystem may identify a version associated with a server subsystem operating the sequencing system to be implemented for servicing the request. The monitor subsystem may allow the server subsystem to be accessed for servicing the request from the client subsystem when the version associated with the client subsystem is compatible with the version associated with the server subsystem. The monitor subsystem may prevent the server subsystem from being accessed when the version associated with the client subsystem is incompatible with the version associated with the server subsystem.

19 Claims, 5 Drawing Sheets

(56) References Cited

U.S. PATENT DOCUMENTS

| | | | |
|---|---|---|---|
| 2005/0226248 A1* | 10/2005 | Modi | H04L 67/14 |
| | | | 370/395.5 |
| 2008/0301668 A1 | 12/2008 | Zachmann | |
| 2011/0131642 A1* | 6/2011 | Hamura | G06F 9/54 |
| | | | 709/227 |
| 2013/0318240 A1* | 11/2013 | Hebert | G06F 9/5038 |
| | | | 709/226 |
| 2014/0088880 A1 | 3/2014 | Shukla et al. | |
| 2021/0057090 A1 | 2/2021 | Gao et al. | |
| 2022/0205033 A1 | 6/2022 | Reed et al. | |

OTHER PUBLICATIONS

"Phase Out Legacy Authentication—The next 9%—Cloudbrothers", Mar. 8, 2021.

* cited by examiner

MULTI-VERSION PROCESSING USING A MONITOR SUBSYSTEM

CROSS-REFERENCE TO RELATED APPLICATIONS

This application claims the benefit of U.S. Provisional Patent Application No. 63/408,235, filed Sep. 20, 2022, which is incorporated by reference herein in its entirety.

BACKGROUND

Sequencing platforms provide fast and accurate secondary and tertiary genomic analysis of sequencing data. The platforms may span hardware and software to deliver a complete sequencing solution. In a single process (SP) environment, a single application may run on a single field-programmable gate array (FPGA) installed on a server device at a time. A single version of the software may be installed on the server device at a given time. Users with specific version requirements may install their desired software versions and run their applications.

In a multi-process (MP) environment, multiple applications can run concurrently on a set of FPGA hardware. Several users can simultaneously run sequencing jobs. Since the sequencing solution may span multiple layers of software and hardware, it is difficult to support client software applications executing different versions of sequencing software on a server device.

SUMMARY

Systems, methods, and apparatus are described herein for monitoring versions of a sequencing system to enable changing of a version of a server subsystem operating the sequencing system to service requests from client subsystems for performing analysis of sequencing data. A monitor subsystem may be utilized for receiving requests from client subsystems. A request may include a version associated with the client subsystem from which the request is received. The monitor subsystem may identify a version associated with a server subsystem operating the sequencing system to be implemented for servicing the request. The monitor subsystem may allow the server subsystem to be accessed for servicing the request from the client subsystem when the version associated with the client subsystem is compatible with the version associated with the server subsystem. The monitor subsystem may prevent the server subsystem from being accessed when the version associated with the client subsystem is incompatible with the version associated with the server subsystem. The monitor subsystem may identify changes in the version associated with the server subsystem for authorizing requests from client subsystems that have been previously prevented from accessing the server subsystem due to the version incompatibility.

The monitor subsystem may continue to authorize requests from client subsystems associated with a compatible version while the server subsystem continues to operate the same version of the sequencing system. When the monitor subsystem determines that the server subsystem, or a process operating thereon, is idle, the monitor subsystem may cause the server subsystem to change versions for processing requests from client subsystems operating utilizing other versions of sequencing applications. The change from the first version to the second version comprises a tear down and a buildup of at least one software layer in a vertical solution stack.

Each version of the server subsystem may comprise different features for bioinformatics components associated with processing different requests. Different bioinformatics components may be utilized by loading the different bioinformatics components into one or more field-programmable gate arrays (FPGAs). The different versions of the server subsystem may support different bioinformatics components to be loaded to the one or more FPGAs for supporting a same or different sequencing task. The sequencing task may include a task performed in secondary analysis or tertiary analysis of sequencing data. The secondary analysis or tertiary analysis comprises alignment, sorting, or variant calling based on the sequencing data.

The monitor subsystem may be a daemon process. The server subsystem may be a daemon process operating at least in part on a client device or a server device. The daemon process may be one of a plurality of predefined daemon processes in the server subsystem.

The monitor subsystem may prevent the server subsystem from being accessed by the client subsystem by preventing an access key from being transmitted to the client subsystem or a connection from being established between the client subsystem and the server subsystem. The monitor subsystem may allow the server subsystem to be accessed by a client subsystem by providing an access key to the client subsystem. The monitor subsystem may notify the server subsystem that the access key has been provided to the client subsystem.

The client subsystem may receive a message indicating that the client subsystem has been blocked. The client subsystem may wait to receive an indication from the monitor subsystem indicating that the request can be processed. The client subsystem may receive the access key and transmit a message to the server subsystem that includes the access key for establishing a connection with the server subsystem.

The request may be received by the monitor subsystem from the client subsystem via a socket. The access may be granted to the server subsystem through the socket via an access key. The monitoring subsystem may monitor signals from child processes to detect a terminal signal for restarting the child process.

DETAILED DESCRIPTION

Figure 1A:
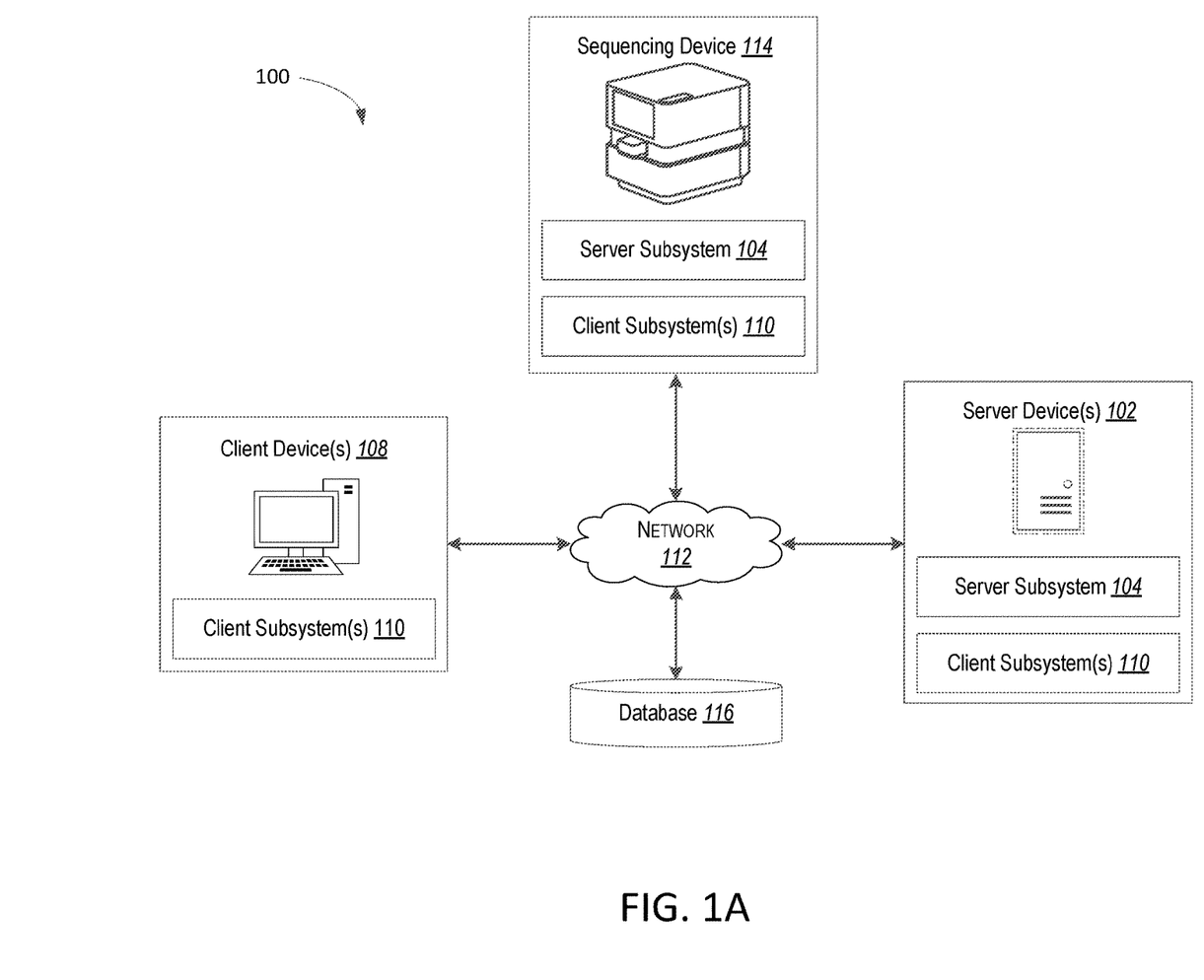
FIG. 1A illustrates a schematic diagram of a system environment.

FIG. 1A illustrates a schematic diagram of a system environment (or "environment") 100, as described herein. As illustrated, the environment 100 includes one or more server device(s) 102 connected to one or more client device(s) 108 and a sequencing device 114 via a network 112.

As shown in FIG. 1A, the server device(s) 102, the client device(s) 108, and the sequencing device 114 may communicate with each other via the network 112. The network 112 may comprise any suitable network over which computing devices can communicate. The network 112 may include a wired and/or wireless communication network. Example wireless communication networks may be comprised of one or more types of radio frequency (RF) communication signals using one or more wireless communication protocols, such as a cellular communication protocol, a wireless local area network (WLAN) or WIFI communication protocol, and/or another wireless communication protocol. In addition, or in the alternative to communicating across the network 112, the server device(s) 102, the client device(s) 108, and/or the sequencing device 114 may bypass the network 112 and may communicate directly with one another.

As further illustrated in FIG. 1A, the environment 100 may include a database 116. The database 116 can store information for being accessed by the devices in the environment 100. The server device(s) 102, the client device(s) 108, and/or the sequencing device 114 may communicate with the database 116 (e.g., directly or via the network 112) to store and/or access information.

As indicated by FIG. 1A, the sequencing device 114 may comprise a device for sequencing a biological sample. The biological sample may include human and/or non-human deoxyribonucleic acid (DNA) to determine individual nucleotide bases of nucleic-acid sequences (e.g., sequencing by synthesis). The biological sample may include human and/or non-human ribonucleic acid (RNA). The sequencing device 114 may analyze nucleic-acid segments and/or oligonucleotides extracted from samples to generate nucleotide reads and/or other data utilizing computer implemented methods and systems described herein either directly or indirectly on the sequencing device 114. More particularly, the sequencing device 114 may receive and analyze, within nucleotide-sample slides (e.g., flow cells), nucleic-acid sequences extracted from samples. The sequencing device 114 may utilize sequencing by synthesis ("SBS") to sequence nucleic-acid segments into nucleotide reads.

As further indicated by FIG. 1A, the server device(s) 102 may generate, receive, analyze, store, and/or transmit digital data, such as data for determining nucleotide-base calls or sequencing nucleic-acid polymers. As shown in FIG. 1A, the sequencing device 114 may generate and send (and the server device(s) 102 may receive) nucleotide reads and/or other sequencing data for being analyzed by the server device(s) 102 for base calling and/or variant calling. The server device(s) 102 may also communicate with the client device(s) 108. In particular, the server device(s) 102 may send data to the client device(s) 108, including sequencing data or other information and the server device(s) 102 may receive input from users via client device(s) 108.

The server device(s) 102 may comprise a distributed collection of servers where the server device(s) 102 include a number of server devices distributed across the network 112 and located in the same or different physical locations. Further, the server device(s) 102 may comprise a content server, an application server, a communication server, a web-hosting server, or another type of server.

As further shown in FIG. 1A, the server device(s) 102 and/or the sequencing device 114 may include a server subsystem 104. The server subsystem 104 may include software and/or hardware utilized by the server device(s) 102 for processing sequencing requests and/or data, as described herein. The server subsystem 104 may be included in a single server device 102 or sequencing device 114, or may be distributed across multiple devices. The server subsystem 104 may include a sequencing system that spans multiple layers of software and/or hardware for servicing requests for sequencing services at the server subsystem 104.

The server subsystem 104 may analyze nucleotide reads and/or other data, such as sequencing metrics received from the sequencing device 114, to determine nucleotide base sequences for nucleic-acid polymers. For example, the server subsystem 104 may receive raw data from the sequencing device 114 and may determine a nucleotide base sequence for a nucleic-acid segment. The server subsystem 104 may process the sequencing data to determine the sequences of nucleotide bases in DNA and/or RNA segments or oligonucleotides. In addition to processing and determining sequences for biological samples, the server subsystem 104 may generate a file for processing and/or transmitting to other devices.

Each client device 108 may generate, store, receive, and/or send digital data. In particular, the client device 108 may receive sequencing metrics from the sequencing device 114. Furthermore, the client device 108 may communicate with the server device(s) 102 to receive one or more files comprising nucleotide base calls and/or other metrics. The client device 108 may present or display information pertaining to the nucleotide-base call within a graphical user interface to a user associated with the client device 108.

The client device(s) 108 illustrated in FIG. 1A may comprise various types of client devices. In examples, the client device 108 may include non-mobile devices, such as desktop computers or servers, or other types of client devices. In other examples, the client device 108 may include mobile devices, such as laptops, tablets, mobile telephones, or smartphones.

As further illustrated in FIG. 1A, each client device 108 may include one or more client subsystem(s) 110. The server device(s) 102 and/or the sequencing device 114 may also, or alternatively, include one or more client subsystem(s). Each client subsystem 110 may include software and/or hardware utilized by a client process for processing sequencing requests and/or data, as described herein. The client subsystem 110 may span multiple layers of software and/or hardware. The client subsystem 110 may be included in a single device or may be distributed across multiple devices.

The client subsystem 110 may comprise a sequencing application. The sequencing application may be a remote application or a native application stored and executed on a local device. The sequencing application may include instructions that (when executed) cause the client device 108 to receive data from the sequencing device 114 and/or the server device(s) 102 and present, for display at the client device 108, data to the user of the client device 108.

Multiple client requests from the client subsystems 110 may be received at the server subsystem 104 for performing sequencing services. The client subsystems 110 that are transmitting the requests may operate using different versions of a sequencing application for analyzing sequencing data. In one example, the different versions of sequencing applications may support different types of analysis for the same or different types of sequencing devices 144. The server subsystem 104 of the server device 102 may load and execute different versions of a sequencing system to support client sequencing applications operating on different versions of software at the client subsystems 110. The different versions of the sequencing system may span multiple layers of software and/or hardware of the server subsystem 104. For example, the different versions of the sequencing system may span multiple software and/or hardware layers of a vertical solution stack.

Figure 1B:
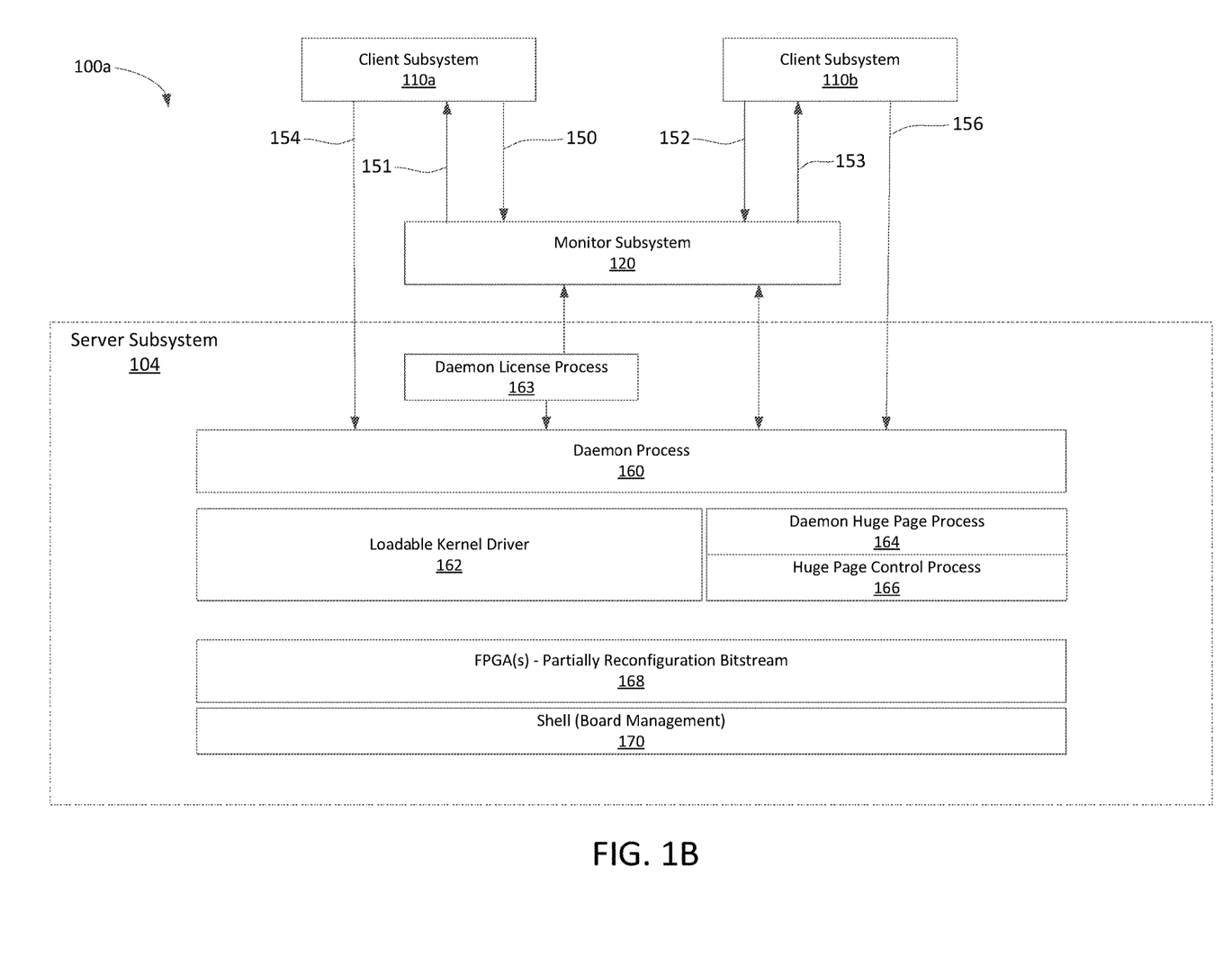
FIG. 1B is a diagram illustrating a system that includes a monitor subsystem that may be utilized in managing requests from client sequencing applications on client subsystems operating on different versions.

Requests received at a server subsystem 104 from client subsystems 110 operating on different versions of software can be appropriately managed using a monitor subsystem. FIG. 1B is a diagram illustrating a system 100a that includes a monitor subsystem 120 that may be utilized in managing requests from client sequencing applications on client subsystems 110a, 110b operating on different versions. For example, the monitor subsystem 120 may receive a request 150 from the client subsystem 110a and a request 152 from the client subsystem 110b. The client subsystems 110a, 110b may each communicate with the monitor subsystem 120 through standard Berkley (BSD) sockets, an address (e.g., IP address and port), or another communication interface that can be accessed via function calls as an endpoint for sending and/or receiving information. The client subsystems 110a, 110b may be executing sequencing applications operating on different versions of software. The monitor subsystem 120 may be a daemon process or other background process executing on one or more server device(s) 102, one or more sequencing devices 114, one or more client devices 108, and/or distributed across server device(s) 102, sequencing device 114, and/or client device(s) 108. The monitor subsystem 120 may be capable of managing the requests 150, 152 for services to be performed by the server subsystem 104 to allow the server subsystem 104 to load and execute different versions of software for operating a sequencing system to support the services in each of the requests 150, 152.

The requests 150, 152 may each include a version identifier, a product identifier, or other information associated with the respective client subsystems 110a, 110b and/or sequencing applications from which each request 150, 152 is received. The monitor subsystem 120 may use the version identifier, the product identifier, and/or the other information in the request 150 to identify the version the client subsystem 110a is utilizing for operation of the sequencing application being executed thereon. The monitor subsystem 120 may use the version identifier, the product identifier, and/or the other information in the request 152 to identify the version the client subsystem 110b is utilizing for operation utilizing for operation of the sequencing application being executed thereon.

The monitor subsystem 120 may be launched upon startup of the sequencing system and/or device(s) on which the monitor subsystem 120 is installed. The monitor subsystem 120 may monitor a version of the sequencing system installed on the server subsystem 104, which may be referred to as a version of the server subsystem 104, to determine whether the version of the sequencing system installed on the server subsystem 104 is compatible with the version of the client subsystems 110a, 110b and/or applications executing thereon from which the requests 150, 152 are being received. Compatible versions may be stored in a file in memory for reference by the monitor subsystem 120. As updated versions of sequencing systems are installed in memory on the one or more devices on which the server subsystem is installed, the file may be updated to identify the compatible versions of client subsystems. The monitor subsystem 120 may be in communication with one or more processes on the server subsystem 104 for identifying the version of one or more layers of software and/or hardware installed in the sequencing system. For example, the server subsystem 104 may program each layer of software and/or hardware in a vertical solution stack according to a different version of the sequencing system.

In one example, a software layer of the server subsystem 104 may include a daemon process 160 with which the monitor subsystem 120 may be in communication. The daemon process 160 may be a background process executing on one or more devices (e.g., server device(s) 102, sequencing devices 114, and/or client devices 108). The daemon process 160 may manage hardware on the one or more devices (e.g., server device(s) 102, sequencing devices 114, and/or client devices 108) in response to requests from client subsystems operating with compatible versions of sequencing applications. The daemon process 160 may be a child service of the monitor subsystem 120 that is launched by the monitor subsystem 120. Monitor subsystem 120 may launch and monitor its child processes for the duration of its run. If any child process dies unexpectedly, then the monitor subsystem 120 may detect the loss and relaunch the child process. The monitor subsystem 120 is able to tear down and build up the services of each layer during version switches by sending commands to one or more child processes (e.g., daemon process 160, daemon license process 163, and/or daemon process 164). The monitor subsystem 120 may query the daemon process 160 for the version of the software and/or hardware layers in the vertical solution stack. In another example, the monitor subsystem 120 may receive push notifications of the version of the software and/or hardware layers in the vertical solution stack.

The server subsystem 104 may include other software processes. For example, the server subsystem 104 may include other background daemon processes in the vertical solution stack. The server subsystem 104 may include a daemon license process 163. The daemon license process 163 may communicate with the monitor subsystem 120 and/or the daemon process 160 to coordinate licenses used by the server subsystem 104. For example, the daemon process 160 may coordinate with daemon license process 163 to validate licenses on behalf of the client subsystem 110. The monitor subsystem 120 may launch the daemon process 160 and/or the daemon license process 163 and monitor these services, as described herein. The server subsystem 104 may also, or alternatively, include a daemon huge page process 164. The daemon huge page process 164 may communicate with the daemon process 160 and/or a huge page control process 166 to manage Huge Pages used for direct memory access (DMA) transfers between host memory and external hardware (e.g., external FPGA hardware). For example, the daemon process 160 may coordinate with daemon huge page process 164 on behalf of the client subsystem 110. The monitor subsystem 120 may launch the daemon process 160 and/or the huge page process 164 and monitor these services, as described herein. The daemon license process 163 and the daemon huge page process 164 may be a child service of the monitor subsystem 120 that is launched by the monitor subsystem 120.

The server subsystem 104 may include a loadable kernel driver 162. For example, the loadable kernel driver 162 may be included in the vertical solution stack. The loadable kernel driver 162 may be an application resident in memory for facilitating interactions between one or more portions of hardware and one or more portions of software. For example, the loadable kernel driver 162 may be in communication with the daemon process 160 and/or one or more portions of programmable hardware for servicing the sequencing system. The loadable kernel driver 162 may support one or more field programmable gate arrays (FP- GAs) comprising a partially reconfiguration bitstream 168. For example, the loadable kernel driver 162 may support one or more FPGAs over Peripheral Component Interconnect Express (PCIe) or another type of serial expansion bus for connecting to one or more peripheral devices.

The hardware layers in the server subsystem 104 may include the programming for one or more hardware layers in the vertical solution stack, such as the FPGAs comprising a partially reconfiguration bitstream 168 and/or a shell 170. The shell 170 may be a hardware layer that includes lower-level code for controlling hardware functionality on the one or more devices (e.g., server device(s) 102, sequencing devices 114, and/or client devices 108) on which the server subsystem 104 is operating. The FPGAs may include more advanced code, such as the partially reconfigurable bitstream 168 for controlling bioinformatics components of the sequencing system. Different sequencing features may be utilized for servicing requests to the sequencing system by the server subsystem 104 uploading different bioinformatic components to the partially reconfiguration bitstream 168 of the FPGA. For example, different images may be uploaded of the partially reconfiguration bitstream 168 for performing different forms of secondary and/or tertiary forms of sequencing analysis. Different sequencing features may be utilized for servicing requests to the sequencing system by the server subsystem 104 uploading different versions of bioinformatic components via the partially reconfiguration bitstream 168 of the FPGA. The different sequencing features may include different algorithms and/or optimization improvements over other versions. Each server subsystem 104 may include one or more FPGAs, which may each be independently partially reconfigured with custom hardware and/or its own shell 170 for board management.

Figure 1C:
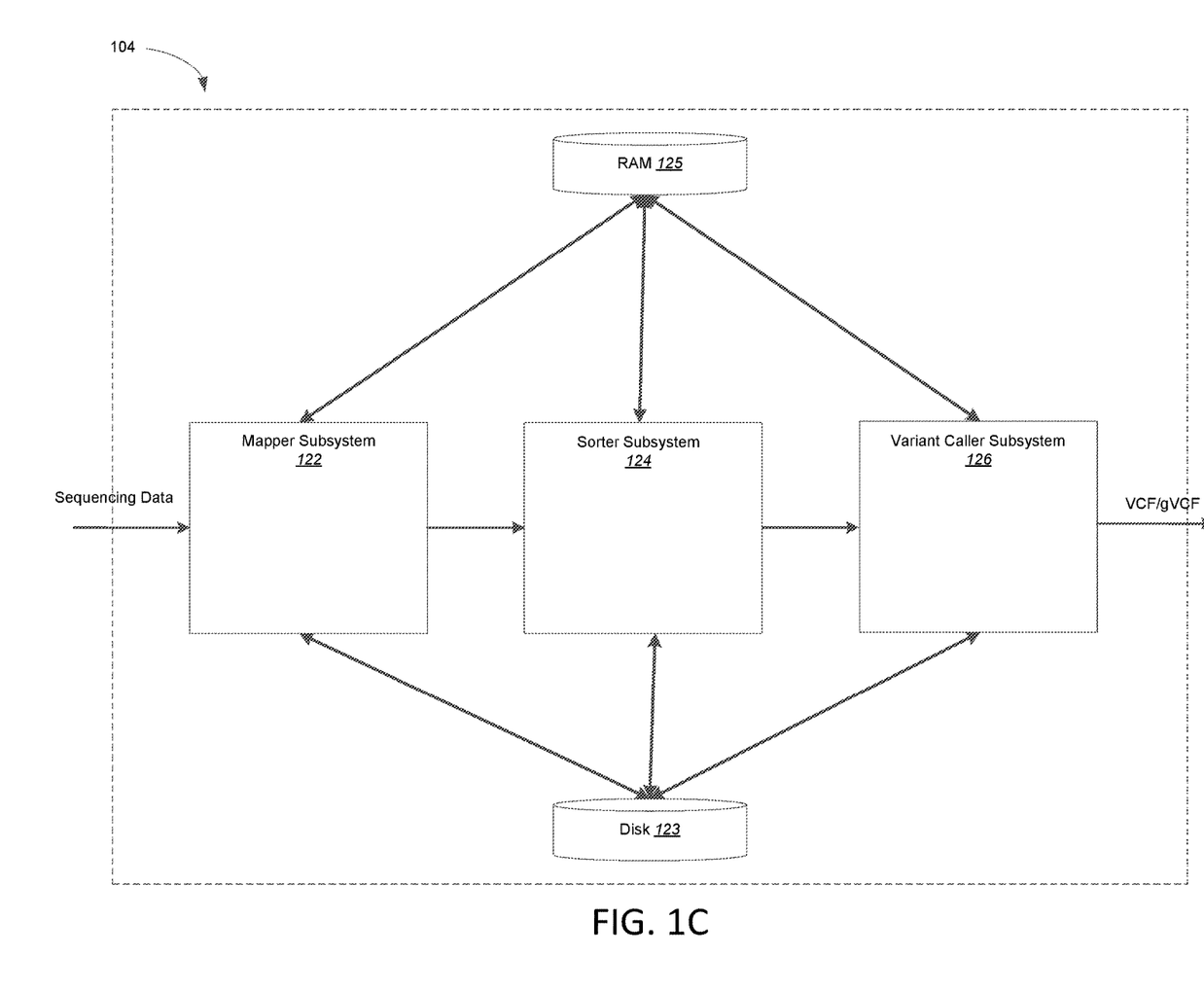
FIG. 1C shows an example of one or more bioinformatics subsystems that may be implemented by the sequencing system operating on the server subsystem for performing secondary and/or tertiary forms of sequencing analysis.

FIG. 1C shows an example of one or more bioinformatics subsystems that may be implemented by the sequencing system operating on the server subsystem 104 for performing secondary and/or tertiary forms of sequencing analysis. As shown in FIG. 1C, the sequencing system may implement a mapper subsystem 122, a sorter subsystem 124, and/or a variant caller subsystem 126. Each bioinformatics subsystem may perform a different sequencing task. The mapper subsystem 122 may be implemented to align the reads in sequencing data received from the sequencing device 114 and/or stored at the one or more devices (e.g., server device(s) 102, sequencing devices 114, and/or client devices 108) on which the server subsystem 104 is operating. The reads in the sequencing data produced by the sequencing device 114 and/or generated and stored in files in memory may not be included in a single sequence with all DNA information. Instead, the sequencing data produced by the sequencing device 114 and/or generated in the files stored in memory may include a number of short subsequences, or reads, with partial DNA information. Read alignment may be performed by the mapper subsystem 122 to map reads to a reference genome and identify the location of each individual read on the reference genome.

After the read alignment is performed at the mapper subsystem 122, the aligned sequencing data may be passed downstream to the sorting subsystem 124 to sort the reads by reference position, and polymerase chain reaction (PCR) or optical duplicates are optionally flagged. An initial sorting phase may be performed by the sorter subsystem 124 on aligned reads returning from the RAM 125. Final sorting and duplicate marking may commence when mapping completes.

The variant caller subsystem 126 may be used to call variants from the aligned and sorted reads in the sequencing data. For example, the variant caller subsystem may receive the sorted BAM file as input and process the reads to generate variant data to be included in a variant call file (VCF) or a genomic variant call format (gVCF) file as output from the variant caller subsystem 126.

Different images may be loaded into a random access memory (RAM) 125 from disk 123 on the server device(s) 102 for each of the subsystems (e.g., mapper subsystem 122, sorter subsystem 124, and variant caller subsystem 126). For example, the RAM 125 may comprise a field programmable gate array (FPGA)-board dynamic RAM (DRAM) on the server device(s) 102 on which different images are loaded from disk 123 for performing different types of analysis using the corresponding subsystem.

Different versions of the subsystems may be loaded into the RAM 125 to support bioinformatics analysis according to different versions of the server subsystem 104 processing requests from client subsystems 110a, 110b. Referring again to FIG. 1B, the different versions of each subsystem may be loaded as the partially reconfiguration bitstream 168 on the FPGAs to enable the server subsystem 104 to perform analysis according to the different bioinformatics subsystems (e.g., mapper subsystem 122, sorter subsystem 124, and variant caller subsystem 126).

As shown in FIG. 1I3, the daemon process 160 may receive requests from authorized client subsystems 110a, 110b and communicate with the other daemon processes 163, 164 and/or the loadable kernel driver 162 for updating the partially reconfiguration bitstream 168 for performing sequencing analysis in response to the requests. Requests may be authorized by the monitor subsystem 120 when the monitor subsystem 120 determines that the requests are being received from a client subsystem 110a that is operating a sequencing application having a compatible version with the current version of the server subsystem 104. The version of the server subsystem 104 may be updated by updating the version of one or more components of the server subsystem 104. For example, the version of the server subsystem 104 may be updated by updating one or more layers of the vertical solution stack, which may include the daemon process 160, the daemon license process 163, the daemon process 164, the huge page control process 166, the loadable kernel driver 162, the partially reconfiguration bitstream 168, and/or the shell 170.

The monitor subsystem 120 may send a command to the daemon process 160 to cause one or more processes, drivers, and/or layers to start, stop, and/or restart. The monitor subsystem 120 may send a command to the daemon process to cause the daemon process 160 to select and load a version of the sequencing system into memory for operating on the server subsystem 104. The monitor subsystem 120 may send a command to the daemon process 160 to load the version of the loadable kernel driver 162 and/or to load the version of the huge page control process 166.

The monitor subsystem 120 may be responsible for authorizing the client subsystems 110a, 110b to transmit the requests 154, 156 to the daemon process 160. The monitor subsystem 120 may authorize the client subsystems 110a, 110b to transmit the requests 154, 156 to the daemon process 160 when the server subsystem 104 is implementing a version of the sequencing system that is compatible with the version of the sequencing application executing on the client subsystems 110a, 110b from which the requests 150, 152 are received. The requests 150, 152 may be triggered by a call from higher level software, which may provide a full path or standard script that may determine the path from a version number of the sequencing application. The trigger may cause the requests 150, 152 to be sent to the monitor subsystem 120 to request permission to continue running. The requests 150, 152 may be blocking calls that return when the permission is obtained or denied. The requests 150, 152 may each include a product identifier, a version identifier, and/or other information associated with the respective client subsystems 110a, 110b from which the requests 150, 152 are received. The monitor subsystem 120 may determine from the information in the requests 150, 152 whether to authorize the client subsystems 110a, 110b to access the daemon process 160.

In one example, the client subsystem 110a and the client subsystem 110b may be operating a sequencing application that are utilizing different versions. The monitor subsystem 120 may receive the request 150 from the client subsystem 110a and determine that the client subsystem 110a is operating a sequencing application with a version that is compatible with the current version of the sequencing system operating on the server subsystem 104. The monitor subsystem 120 may authorize the client subsystem 110a to send the request 154 to the daemon process 160 for accessing the daemon process 160 and/or having the request serviced by the server subsystem 104. If the monitor subsystem 120 determines that the version of the client subsystem 110a from which the request 150 is received is compatible with the version of the server subsystem 104, the monitor subsystem 120 may send an authorization message 151 to the client subsystem 110a granting access to the server subsystem 104 and/or the daemon process 160. The authorization message may include an acknowledgement in response to the request, or the monitor subsystem 120 may send an acknowledgement of receipt of each request without providing authorization. The authorized client subsystem 110a may be registered in memory with the monitor subsystem 120 as being authorized for being serviced by the server subsystem 104. The authorization message 151 may include an access key for accessing the server subsystem 104 and/or the daemon process 160. The access key may also be provided to the daemon process 160 in a notification message notifying the daemon process that the client subsystem 110a has been authorized, such that the daemon process 160 may identify the authorized client subsystem 110a. In another example, the monitor subsystem 120 may provide the daemon process 160 with the identifier of the client subsystem 110a or other information associated with the client subsystem 110a to indicate that the client subsystem 110a has been authorized. The daemon process 160 may receive the request 154 and identify that the request is received from an authorized client subsystem 110a (e.g., based on the access key or other information in the request 154). After the daemon process 160 identifies that the request 154 is being received from an authorized client subsystem 110a, the daemon process 160 may establish a connection with the client subsystem 110a, register the client subsystem 110a in memory, and begin servicing the request 154 by communicating with other processes, drivers, and/or layers of the vertical solution stack in the server subsystem 104. The connection may be established through standard Berkley (BSD) sockets or another communication interface, an address (e.g., IP address and port), or another communication interface that can be accessed via function calls as an endpoint for sending and/or receiving information The daemon process 160 may communicate with the loadable kernel driver 162 to service one or more requests from client subsystems. For example, the loadable kernel driver 162 may have one or more FPGAs under its control. The loadable kernel driver 162 may support the one or more FPGAs over PCIe. A bioinformatics subsystem (e.g., mapper subsystem 122, sorter subsystem 124, and variant caller subsystem 126) may be loaded into each FPGA for processing the requests. Different bioinformatics subsystems may be loaded into different FPGAs for processing different requests simultaneously. As such, the requests may be processed in batches using parallel processing across multiple FPGAs. Each of the bioinformatics subsystems may be operating in a version that is compatible with the version of the requests from the client subsystems. Workload management and dispatching client jobs to the FPGAs may be performed by daemon process 160 after receiving corresponding requests. The loadable kernel driver 162 may enumerate the devices and provide communication paths between daemon process 160 and the appropriate FPGAs.

The monitor subsystem 120 may receive the request 152 from the client subsystem 110b and determine that the client subsystem 110b is operating a sequencing application with a version that is incompatible with the current version of the sequencing system operating on the server subsystem 104. Since the client subsystem 110b is operating a sequencing application with a version that is incompatible with the current version of the server subsystem 104, the client subsystem 110b may be blocked and/or the request 152 may be queued for being serviced at a later time. Requests that are compatible with different versions of the server subsystem than the one that is currently loaded may be queued in different queues or in the same queue. The client subsystem 110b may be blocked and/or the request 152 may be queued until the sequencing system of the server subsystem 104 is operating a version that is compatible with the version of the sequencing application operating on the client subsystem 110b. The monitor subsystem 120 may fail to provide an access key to the client subsystem 110b preventing the client subsystem 110b from being able to access the daemon process 160 of the server subsystem 104 until the server subsystem 104 is operating a version that is compatible with the version of the sequencing application operating on the client subsystem 110b. The monitor subsystem 120 may send a message to the client subsystem configured to cause the client subsystem to wait for authorization and/or transmit a subsequent request at a later time.

The monitor subsystem 120 may monitor a status of the server subsystem 104 to determine an appropriate time at which to authorize the client subsystem 110b to access the server subsystem 104. For example, the monitor subsystem 120 may monitor a status of the client subsystems, such as the client subsystem 110a, that have been authorized to access the server subsystem 104 and/or that have been registered in memory as being authorized. The monitor subsystem 120 may monitor the status of one or more child processes (e.g., daemon process 160, daemon license process 163, and/or daemon process 164) that are processing the requests from the client subsystems that have been authorized to access the server subsystem 104 and identify a termination signal from the one or more child processes that are servicing the requests of the client subsystems. The termination signal may identify a completion of the services being requested from the server subsystem 104 (e.g., completion of the services and/or tasks identified in the request 154) or an abnormal termination for which the services being requested have failed to complete. If any child process has a termination without the monitor subsystem 120 explicitly signaling the child process to be stopped, then the monitor subsystem 120 is notified of the child process termination by another service. For example, the monitor subsystem 120 may receive the PID (process identifier) and the cause of termination from the other service operating on the same device. The monitor subsystem 120 may log the PID and/or cause of the termination and relaunch the process. If the monitor subsystem 120 identifies an abnormal termination, the monitor subsystem 120 may automatically reset software and/or hardware managed by the server subsystem 104. For example, the monitor subsystem 120 may send a signal to the daemon process 160 to cause the daemon process 160 to reset hardware, child processes of the monitor subsystem 120, processes, drivers, and/or other software in the vertical solution stack. The hardware and/or software may be restarted and the hardware and/or software may be restarted for being operated with the same version of software loaded into the server subsystem 104 before the restart. After the hardware and/or software have been restarted, the server subsystem 104 may continue to service the requests that are compatible with the current version of the server subsystem 104.

The server subsystem 104 may be operating in an active state when one or more processes therein are servicing a request from an authorized client subsystem, such as the client subsystem 110a. While the server subsystem 104 is in the active state and is servicing the request 154 from the client subsystem 110a, the monitor subsystem 120 may continue to receive requests from other client subsystems. Requests from client subsystems that are operating sequencing applications in a version that is incompatible with the server subsystem 104 may continue to be blocked and/or queued for being serviced at a later time. Requests from client subsystems that are operating sequencing applications in a version that is compatible with the server subsystem 104 may continue to be authorized (e.g., while the request 152 from the client subsystem 110b is queued) and the server subsystem 104 may remain in the active state until a termination signal is identified. When the active state of each of the previously authorized client subsystems have terminated, the server subsystem 104 and/or one or more processes therein may enter an idle state.

The monitor subsystem 120 may communicate with one or more processes of the server subsystem 104 for determining whether the server subsystem 104 and/or one or more processes therein are in an active state or an idle state. In one example, the monitor subsystem 120 may be in communication with the daemon process 160 for determining an active state and an idle state of the server subsystem 104 and/or one or more processes therein. The monitor subsystem 120 may send a command to the daemon process 160 for requesting the current status of the processing of each of the requests from client subsystems. The monitor subsystem 120 may send a command to the daemon process 160 to query the current version of the server subsystem 104.

The monitor subsystem 120 may determine from the daemon process 160 when the daemon process 160 and/or other processes or layers in the vertical solution stack are active or idle. When the monitor subsystem 120 determines from the daemon process 160 that the daemon process 160 and/or other processes or layers in the vertical solution stack have ceased servicing client subsystems and entered the idle state for a period of time, the monitor subsystem 120 may change the version of the sequencing system being operated by the server subsystem 104 and authorize requests from client subsystems operating a sequencing application according to a compatible version.

The monitor subsystem 120 may select the next version of the sequencing system. The monitor subsystem 120 may select the next version of the sequencing system in response to user input from the client device(s) 108. The user input may identify a selected version of the server subsystem. The user input may be sent in response to a query from the monitor subsystem 120. The monitor subsystem 120 may automatically select the next version based on the versions in the requests that have been previously received from client subsystems. The monitor subsystem 120 may select the version based on the version in the first request that was blocked and/or queued. For example, the monitor subsystem 120 may select a version of the server subsystem 104 to be loaded into memory that is compatible with the version identified in the request 152 received from the client subsystem 110b, which was previously determined to be incompatible. The monitor subsystem 120 may continue to select the versions based on an order of the requests that have been blocked and/or queued. The monitor subsystem 120 may select the version based on the number of requests that have been blocked and/or queued. For example, the monitor subsystem 120 may select the next version for being loaded into memory for the server subsystem 104 by identifying the version that is compatible with the largest number of blocked or queued requests from client subsystems.

The monitor subsystem 120 may communicate with one or more processes of the server subsystem 104 for orchestrating the change in version of the sequencing system operating on the server subsystem 104. In one example, the monitor subsystem 120 may be in communication with the daemon process 160 for restarting one or more portions of hardware and/or software for changing the version of the server subsystem 104. One or more layers (e.g., each layer) of the vertical solution stack of the server subsystem 104 may be torn down and rebuilt for the next version. The monitor subsystem 120 may send a command to the daemon process 160 to cause the daemon process to remove one or more processes, drivers, and/or layers currently loaded into memory. The command from the monitor subsystem 120 may be received by one or more child processes (e.g., daemon process 160) to cause one or more layers to tear down the current version services by bringing down the services supporting the current version before switching to another version. The monitor subsystem 120 may send a command that is received by one or more child processes (e.g., daemon process 160) to cause one or more layers to be rebuilt by restarting a next version of services to support the next version. For example, the monitor subsystem 120 may send one or more commands to one or more child processes (e.g., daemon process 160) that are in communication with one or more other layers of the vertical solution stack for tearing down and rebuilding the services supported by each layer. The one or more child processes (e.g., daemon process 160) may reset the FPGAs and/or load new programmable hardware into the FPGAs to enable a complete solution comprising version changes in hardware and/or software.

The processes, drivers, and/or layers that are torn down and/or rebuilt when changing versions may be predefined or may be selected dynamically. For example, the monitor subsystem 120 may select the processes, drivers, and/or layers that are to be torn down and/or rebuilt may be based on the previous version of the server subsystem 104 and the next version. Each version of the sequencing system may be stored in memory with a version file that may be accessed by the monitor subsystem 120 for identifying the portions of the server subsystem 104 to be torn down and/or built back up for supporting the next version of the sequencing system being operated by the server subsystem 104. Each version of the sequencing system may include metadata or other information that can be read by the monitor subsystem for selecting the processes, drivers, and/or layers of the vertical solution stack for being loaded into memory. For example, each version of the sequencing system may provide a manifest that may be used by the monitor subsystem 120 to select the processes, drivers, and/or layers to be loaded into memory for each version. Each manifest may include a version number corresponding to the version of the sequencing system for which the manifest is provided. The manifest may include a manifest version itself, as each manifest may have different versions. The manifest may include a version of one or more processes and/or drivers for being loaded into memory for building the vertical solution stack. For example, the manifest may include a version of the daemon process 160, a version of the daemon license process 163 and/or a version of the daemon huge page process 164 for supporting a version of the server subsystem 104. The manifest may include a driver version and/or location of kernel objects for the loadable kernel driver 162. For example, the location of the kernel objects may include version directory or an alternate location (e.g., when multiple versions of kernel driver are supported). The manifest may include the version of the client subsystems and/or sequencing applications operating thereon that are compatible with the version of the server subsystem 104. The manifest may include a version of the partially reconfiguration bitstream 168 and/or subsystems that may be loaded therein (e.g., mapper subsystem 122, sorter subsystem 124, and/or variant caller subsystem 126). The manifest may include a version of the shell 170. Some processes, drivers, and/or layers may remain static from version to version, which may support backwards compatibility with legacy systems. For example, the loadable kernel driver 162 and/or the shell 170 may remain static between versions for supporting the processes in other layers of the vertical solution stack.

After the monitor subsystem 120 selects the version of the sequencing system being operated by the server subsystem 104 and loads the processes, drivers, and/or layers of the selected version of the sequencing system, the processes may be started and/or drivers may be loaded in the vertical solution stack for servicing requests that are compatible with the selected version of the sequencing system. In one example, when the monitor subsystem 120 determines that the version of the sequencing system operating on the server subsystem 104 is compatible with the version of the sequencing application of the client subsystem 110*b*, the monitor subsystem 120 may authorize the client subsystem 110*b* to access the server subsystem 104 and/or one or more processes thereon. The monitor subsystem 120 may authorize the client subsystem 110*b* to send the request 156 to the daemon process 160 for accessing the daemon process 160 and/or having the request serviced by the server subsystem 104. After the monitor subsystem 120 determines that the version of the client subsystem 110*b* from which the request 152 is received is compatible with the version of the server subsystem 104, the monitor subsystem 120 may send an authorization message 153 to the client subsystem 110*b* granting access to the server subsystem 104 and/or the daemon process 160. The authorization message may include an acknowledgement in response to the request, or the monitor subsystem 120 may send an acknowledgement of receipt of each request without providing authorization. The authorized client subsystem 110*b* may be registered in memory with the monitor subsystem 120 as being authorized for being serviced by the server subsystem 104. The authorization message 153 may include an access key for accessing the server subsystem 104 and/or the daemon process 160. The access key may also be provided to the daemon process 160 in a notification message notifying the daemon process that the client subsystem 110*b* has been authorized, such that the daemon process 160 may identify the authorized client subsystem 110*b*. In another example, the monitor subsystem 120 may provide the daemon process 160 with the identifier of the client subsystem 110*b* or other information associated with the client subsystem 110*b* to indicate that the client subsystem 110*b* has been authorized. The daemon process 160 may receive the request 156 and identify that the request is received from an authorized client subsystem 110*b* (e.g., based on the access key or other information in the request 156). After the daemon process 160 identifies that the request 156 is being received from an authorized client subsystem 110*b*, the daemon process 160 may establish a connection with the client subsystem 110*b*, register the client subsystem 110*b* in memory, and begin servicing the request 156 by communicating with other processes, drivers, and/or layers of the vertical solution stack in the server subsystem 104. For example, the daemon process 160 may use an inter-process communication (IPC) messaging protocol over BSD sockets to communicate with its clients. Each client may register with the daemon process 160 by connecting to a Unix domain socket address. This channel may be open for the clients to send messages to daemon process 160 to which the daemon process 160 may respond after completing the client's request.

Figure 2:
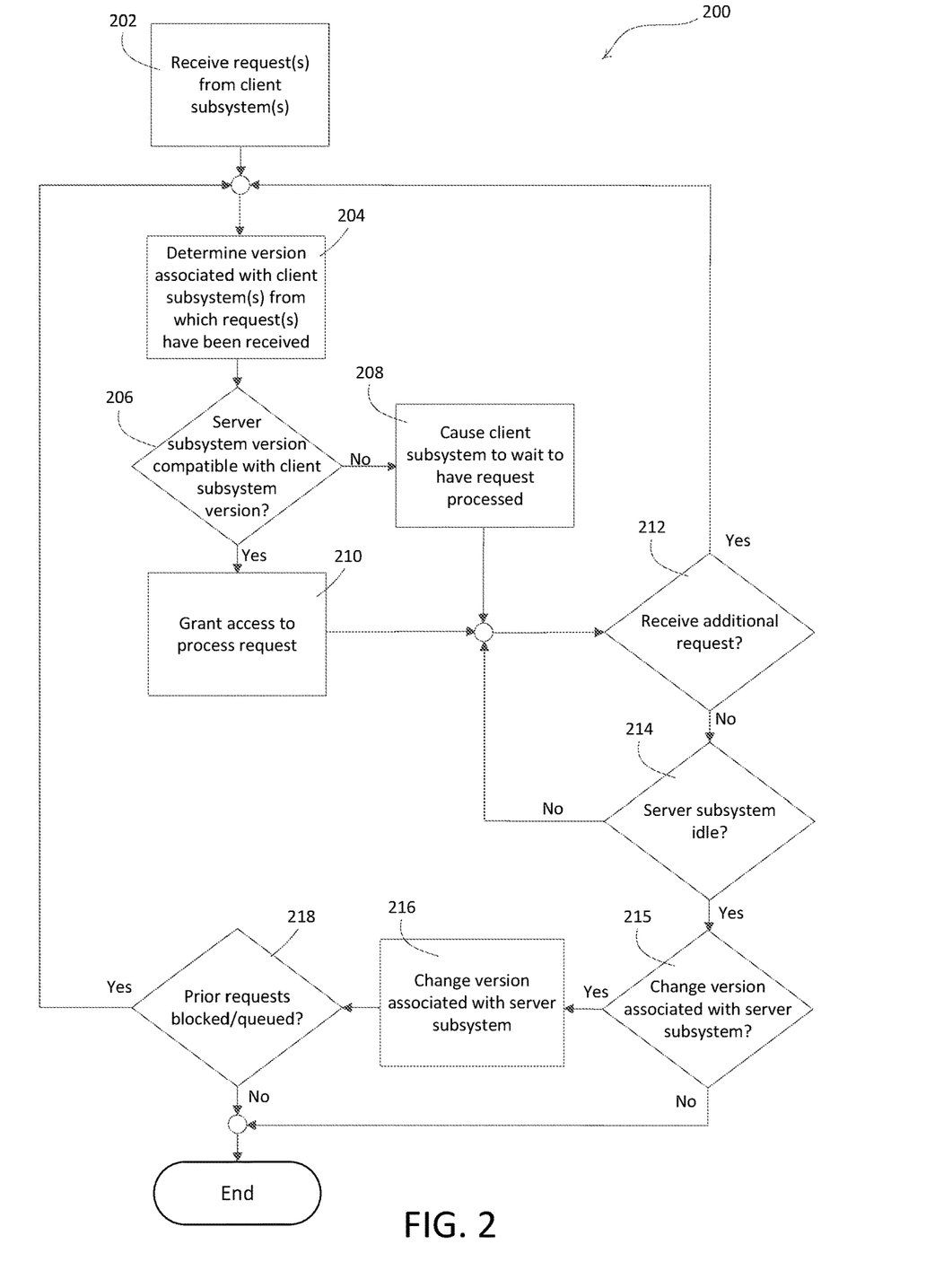
FIG. 2 is a flowchart depicting an example procedure for monitoring versions of a server subsystem and processing requests from compatible client subsystems.

FIG. 2 is a flowchart depicting an example procedure 200 for monitoring versions of a server subsystem and processing requests from compatible client subsystems. The one or more portions of the procedure 200 may be performed by one or more computing devices or systems. For example, the one or more portions of the procedure 200 may be performed by one or more server devices, one or more sequencing devices, and/or one or more client devices. One or more portions of the procedure 200 may be stored in memory as computer-readable or machine-readable instructions that may be executed by a processor of the one or more computing devices. One or more portions of the procedure 200 may be performed by one or more subsystems operating on a client device, a sequencing device, and/or a server device. For example, one or more portions of the procedure may be performed by a client subsystem, a server subsystem, and/or a monitor subsystem, as described herein. Though portions of the procedure 200 may be described herein as being performed by a monitor subsystem, the procedure 300, or portions thereof, may be performed by another subsystem operating on a computing device or distributed across multiple computing devices, such as one or more client computing devices, one or more sequencing devices, and/or one or more server computing devices.

The procedure 200 may begin at 202. As shown in FIG. 2, at 202 the monitor subsystem may receive one or more requests from one or more client subsystems. The requests may be received individually or in a batch for being processed by the sequencing system of the server subsystem. The request may comprise a product identifier, a version identifier, and/or other information associated with the client subsystem from which the request is received. At 204, the monitor subsystem may determine a version associated with the client subsystem from which the request is received. For example, the monitor subsystem may determine the version based on the product identifier, the version identifier, or the other information associated with the client subsystem. At 206, the monitor subsystem may determine whether a version associated with the server subsystem is compatible with the version associated with the client subsystem. For example, the monitor subsystem may receive an indication of a version of a sequencing system operating on the server subsystem to determine whether the version of the sequencing system is compatible with a version of a sequencing application operating on the client subsystem. The indication of the version of the sequencing system operating on the server subsystem may be received from a daemon process (e.g., in response to a request) operating on the server subsystem. Compatible versions may be indicated by the same version number/identifier, or a different version number/identifier indicated in memory as being compatible with one or more features of another version number/identifier. The version may be a version of one or more processes, drivers, and/or layers of a vertical solution stack. If the version associated with the server subsystem is compatible with the version associated with the client subsystem, the client subsystem may be granted access to the server subsystem and/or one or more processes thereon for processing the request at 210. The request may be processed by loading one or more bioinformatics subsystems (e.g., mapper subsystem, sorter subsystem, and/or variant caller subsystem) into one or more FPGAs for performing secondary and/or tertiary analysis of sequencing data.

If the version associated with the server subsystem is incompatible with the version associated with the client subsystem, the monitor subsystem may cause the client subsystem to wait to have the request processed at 208. For example, the monitor subsystem may block the request to prevent access to the server subsystem and/or queue the request for being processed at a later time. The monitor subsystem may determine, at 212, whether additional requests have been received while the server subsystem is operating its sequencing system in the current version. For example, additional requests may continue to be received by the monitor subsystem while the server subsystem is processing one or more requests from client subsystems that have been granted access at 210 and/or before the server subsystem has changed versions. If an additional request is received at 212 by the monitor subsystem, the request may be processed at 204 to determine a version associated with the client subsystem for determining whether to grant access to the request at 210. The monitor subsystem may determine, at 214, whether the server subsystem is idle. The server subsystem may be determined to be idle when one or more processes operating the sequencing system thereon are determined to be idle. The monitor subsystem may request the status of one or more processes of the server subsystem. In one example, the monitor subsystem may send a message to the daemon process of the server subsystem to determine a status of the processing of the requests from client subsystems. The daemon process may send a termination signal at the end of processing the requests from one or more client subsystems. The monitor subsystem may monitor the status of the requests and identify a termination signal for each previously authorized request. If the server subsystem is determined to still be active and processing requests from client subsystems, the monitor subsystem may continue to monitor for additional requests at 212 and/or monitor the server subsystem for identifying an idle state at 214.

If the server subsystem and/or one or more processes operating thereon are determined to be idle, the monitor subsystem may determine whether to change a version associated with the server subsystem at 215. The monitor subsystem may identify an indication for changing the version associated with the server subsystem prior to making the change. For example, the monitor subsystem may determine to change the version associated with the server subsystem if additional requests have been received from client subsystems that are associated with incompatible versions that have been blocked and/or queued. The monitor subsystem may also, or alternatively, determine to change the version associated with the server subsystem if a user input has been received from a sequencing application operating on a client device that is instructing the monitor subsystem to change the version of the server subsystem. If the monitor subsystem decides to maintain the version associated with the server subsystem (e.g., as no indication is identified for changing the version associated with the server subsystem), the procedure 200 may end.

If the monitor subsystem decides to change the version associated with the server subsystem, the monitor subsystem may cause the server subsystem to change versions at 216 for processing requests from client subsystems that are compatible with another version of the server subsystem. The monitor subsystem may send a command to the server subsystem and/or one or more processes operating thereon to cause the server subsystem to stop executing one or more processes prior to changing the version. The monitor subsystem may send a command to the server subsystem and/or one or more processes operating thereon to cause the server subsystem to change versions for processing requests from client subsystems. The commands may be sent to a daemon process operating on the server subsystem to cause the version of one or more processes, drivers, and/or layers of a vertical solution stack to be changed according to the next version. The next version may be selected by the monitor subsystem. For example, the next version may be selected based on user input received from a client device operating a sequencing application. The next version may also, or alternatively, be selected automatically based on a version of previously blocked and/or queued requests from client subsystems. The monitor subsystem may select the version based on the version in the first request that was blocked and/or queued or an order of requests that have been blocked and/or queued in time. The monitor subsystem may select the version based on the number of requests that have been blocked and/or queued. For example, the monitor subsystem may select the next version for being loaded into memory for the server subsystem by identifying the version that is compatible with the largest number of blocked and/or queued requests from client subsystems.

After the version associated with the server subsystem has been changed to the next version, the monitor subsystem may send a command to the server subsystem and/or one or more processes thereon (e.g., daemon process) to begin executing. At 218, the monitor subsystem may determine whether prior requests were received that have been blocked and/or queued for being processed by the server subsystem. If prior requests have not been received for processing by the server subsystem, the procedure 200 may end. If prior requests were received that have been blocked and/or queued, the monitor subsystem may determine whether the version of one or more prior requests are compatible with the server subsystem at 204. The monitor subsystem may send a message to client subsystems to inform the client subsystem that the server subsystem is ready to service its request. The monitor subsystem may send request that the client subsystems resend their requests for being processed. The monitor subsystem may grant access to process the requests at 210 that are associated with client subsystems determined to be compatible. The monitor subsystem may continue to block and/or queue requests that are incompatible with the current version associated with the server subsystem after the version has been changed. After each of the requests have been processed as described herein, the procedure may end.

Figure 3:
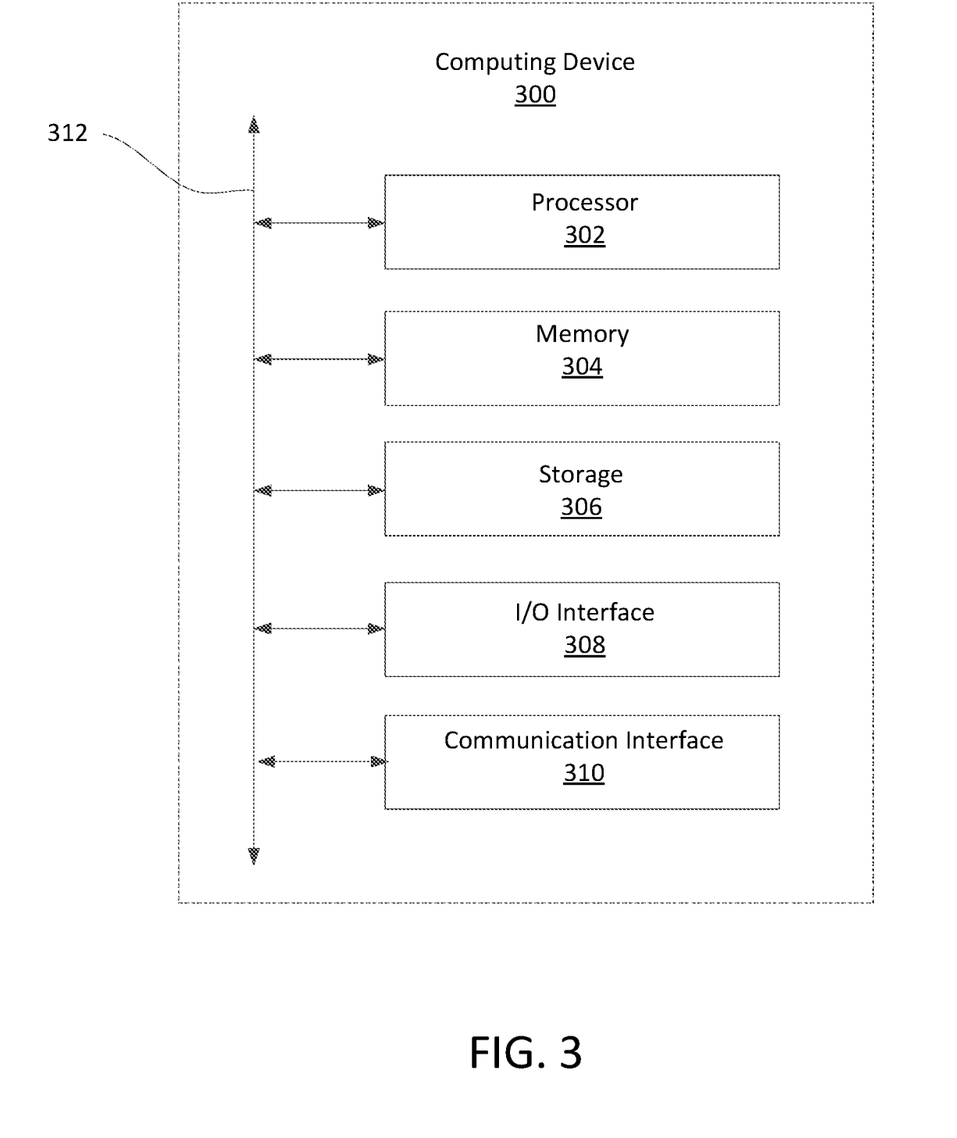
FIG. 3 is a block diagram of an example computing device.

FIG. 3 is a block diagram illustrating an example computing device 300 (or computing system). One or more computing devices such as the computing device 300 may implement one or more features for monitoring and/or changing a version of a sequencing system to service requests from a sequencing application as described herein. For example, the computing device 300 may comprise one or more of the sequencing device 114, the client device(s) 108, and/or the server device(s) 102 shown in FIG. 1A. As shown by FIG. 3, the computing device 300 may comprise a processor 302, a memory 304, a storage device 306, an I/O interface 308, and a communication interface 310, which may be communicatively coupled by way of a communication infrastructure 312. The computing device 300 may include fewer or more components than those shown in FIG. 3.

The processor 302 may include hardware for executing instructions, such as those making up a computer application or system. In examples, to execute instructions for operating as described herein, the processor 302 may retrieve (or fetch) the instructions from an internal register, an internal cache, the memory 304, or the storage device 306 and decode and execute the instructions. The memory 304 may be a volatile or non-volatile memory used for storing data, metadata, computer-readable or machine-readable instructions, and/or programs for execution by the processor(s) for operating as described herein. The storage device 306 may include storage, such as a hard disk, flash disk drive, or other digital storage device, for storing data or instructions for performing the methods described herein.

The I/O interface 308 may allow a user to provide input to, receive output from, and/or otherwise transfer data to and receive data from the computing device 300. The I/O interface 308 may include a mouse, a keypad or a keyboard, a touch screen, a camera, an optical scanner, network interface, modem, other known I/O devices or a combination of such I/O interfaces. The I/O interface 308 may include one or more devices for presenting output to a user, including, but not limited to, a graphics engine, a display (e.g., a display screen), one or more output drivers (e.g., display drivers), one or more audio speakers, and one or more audio drivers. The I/O interface 308 may be configured to provide graphical data to a display for presentation to a user. The graphical data may be representative of one or more graphical user interfaces and/or any other graphical content.

The communication interface 310 may include hardware, software, or both. In any event, the communication interface 310 may provide one or more interfaces for communication (such as, for example, packet-based communication) between the computing device 300 and one or more other computing devices and/or networks. The communication may be a wired or wireless communication. As an example, and not by way of limitation, the communication interface 310 may include a network interface controller (NIC) or network adapter for communicating with an Ethernet or other wire-based network or a wireless NIC (WNIC) or wireless adapter for communicating with a wireless network, such as a WI-FI.

Additionally, the communication interface 310 may facilitate communications with various types of wired or wireless networks. The communication interface 310 may also facilitate communications using various communication protocols. The communication infrastructure 312 may also include hardware, software, or both that couples components of the computing device 300 to each other. For example, the communication interface 310 may use one or more networks and/or protocols to enable a plurality of computing devices connected by a particular infrastructure to communicate with each other to perform one or more aspects of the processes described herein. To illustrate, the sequencing process may allow a plurality of devices (e.g., a client device, sequencing device, and server device(s)) to exchange information such as sequencing data and error notifications.

In addition to what has been described herein, the methods and systems may also be implemented in a computer program(s), software, or firmware incorporated in one or more computer-readable media for execution by a computer(s) or processor(s), for example. Examples of computer-readable media include electronic signals (transmitted over wired or wireless connections) and tangible/non-transitory computer-readable storage media. Examples of tangible/non-transitory computer-readable storage media include, but are not limited to, a read only memory (ROM), a random-access memory (RAM), removable disks, and optical media such as CD-ROM disks, and digital versatile disks (DVDs).

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure.

What is claimed is:

1. A system comprising:
   at least one memory having computer-readable instructions stored thereon; and
   at least one processor, the at least one processor being configured, in response to the computer-readable instructions, to:
   receive, via a monitor subsystem, a request from a client subsystem, wherein the request is a request for performing secondary analysis or tertiary analysis of sequencing data, wherein the request comprises a version associated with the client subsystem;
   determine a first version associated with a server subsystem to be implemented for servicing the request;
   determine that the version associated with the client subsystem is incompatible with the first version associated with the server subsystem currently implemented for servicing the request;
   in response to the determination that the version associated with the client subsystem is incompatible with the first version associated with the server subsystem, prevent the server subsystem from being accessed by the client subsystem;
   identify that the server subsystem is idle after processing each request from client subsystems associated with a compatible version;
   cause the server subsystem to perform a change from the first version to a second version;
   determine that the second version associated with the server subsystem is compatible with the version associated with the client subsystem; and
   allow the client subsystem to access the server subsystem for servicing the request.

2. The system of claim 1, wherein the request from the client subsystem is a first request, and wherein the client subsystem is a first client subsystem, the at least one processor being further configured, in response to the computer-readable instructions, to:

receive, via the monitor subsystem, a second request from a second client subsystem, wherein the second request comprises a version associated with the second client subsystem;

while the server subsystem is operating in the first version, determine that the version associated with the second client subsystem is compatible with the first version associated with the server subsystem; and allow the server subsystem to be accessed by the second client subsystem for the second request.

3. The system of claim 1, wherein each version of the server subsystem comprises different features for bioinformatics components associated with processing different requests for the secondary analysis or the tertiary analysis.

4. The system of claim 1, wherein different bioinformatics components are utilized by loading the different bioinformatics components into one or more field-programmable gate arrays (FPGAs).

5. The system of claim 1, wherein the change from the first version to the second version comprises a tear down and a buildup of at least one software layer in a vertical solution stack.

6. The system of claim 5, wherein the first version and the second version support different bioinformatics components to be loaded to one or more FPGAs for supporting a same or different sequencing task.

7. The system of claim 6, wherein the sequencing task comprises a task performed for the secondary analysis or the tertiary analysis of the sequencing data.

8. The system of claim 1, wherein the secondary analysis or the tertiary analysis comprises alignment, sorting, or variant calling based on the sequencing data.

9. The system of claim 1, wherein the monitor subsystem is a daemon process.

10. The system of claim 1, wherein the server subsystem is a daemon process, and wherein the server subsystem is configured to manage hardware on the system for servicing a sequencing application operating on one or more client subsystems.

11. The system of claim 10, wherein the daemon process is one of a plurality of predefined daemon processes in the server subsystem.

12. The system of claim 1, wherein the at least one processor being configured to prevent the server subsystem from being accessed by the client subsystem for the request further comprises the at least one processor being configured to:

prevent an access key from being transmitted to the client subsystem or a connection from being established between the client subsystem and the server subsystem.

13. The system of claim 1, wherein the at least one processor being configured to allow the server subsystem to be accessed by the client subsystem further comprises the at least one processor being configured to:

provide, via the monitor subsystem, an access key to the client subsystem; and notify, via the monitor subsystem, the server subsystem that the access key has been provided to the client subsystem.

14. The system of claim 13, wherein the at least one processor being configured to notify the server subsystem further comprises the at least one processor being configured to provide the access key to the server subsystem.

15. The system of claim 13, wherein the processor is further configured, via the computer-readable instructions, to:

receive a message via the client subsystem indicating that the client subsystem has been blocked; and wait to receive an indication via the client subsystem from the monitor subsystem indicating that the request can be processed.

16. The system of claim 13, wherein the processor is further configured, via the computer-readable instructions, to:

receive the access key via the client subsystem; and transmit a message to the server subsystem that includes the access key for establishing a connection with the server subsystem.

17. The system of claim 1, wherein the processor is further configured, via the computer-readable instructions, to send an acknowledgement to the client subsystem in response to the request.

18. The system of claim 1, wherein the processor is further configured, via the computer-readable instructions, to receive the request from the client subsystem via a socket, and grant access to the server subsystem through the socket via an access key.

19. The system of claim 1, wherein the processor is further configured, via the computer-readable instructions, to:

monitor, by the monitor subsystem, signals from at least one child process;

detect a terminal signal via the at least one child process; and automatically restart the at least one child process.

* * * * *